United States Patent
Baxter et al.

(10) Patent No.: US 6,383,813 B1
(45) Date of Patent: May 7, 2002

(54) MICROFABRICATION OF A NUCLEAR TRANSFER ARRAY FOR HIGH-THROUGHPUT ANIMAL CLONING

(75) Inventors: Gregory T. Baxter, Ithaca, NY (US); Richard C. Kuo, Fremont, CA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/662,342

(22) Filed: Sep. 14, 2000

Related U.S. Application Data

(60) Provisional application No. 60/153,677, filed on Sep. 14, 1999.

(51) Int. Cl.[7] ............................................... C12N 15/63
(52) U.S. Cl. .................... 435/455; 435/285.1; 435/455; 935/85; 935/93
(58) Field of Search ............................. 435/455, 285.1; 935/85, 93

(56) References Cited

U.S. PATENT DOCUMENTS

| | | |
|---|---|---|
| 4,247,646 A | 1/1981 | Berky et al. |
| 4,304,865 A | 12/1981 | O'Brien et al. |
| 4,664,097 A | 5/1987 | McGrath et al. |
| 4,994,384 A | 2/1991 | Prather et al. |
| 5,057,420 A | 10/1991 | Massey |
| 5,073,482 A | 12/1991 | Goldstein |
| 5,120,657 A | 6/1992 | McCabe et al. |
| 5,262,128 A | 11/1993 | Leighton et al. |
| 5,453,366 A | 9/1995 | Sims et al. |

FOREIGN PATENT DOCUMENTS

| | | | |
|---|---|---|---|
| WO | WO 00/65137 | * | 11/2000 |

OTHER PUBLICATIONS

Wilmut, I., et al., "Viable Offspring Derived From Fetal and Adult Mammalian Cells," 1997, Nature, p. 810–813.
Wakayama, T. et al., "Full–Term Development of Mice from Enucleated Oocytes Injected with Cumulus Cell Nuclei," 1998, Nature, p. 369–374.
Schnieke, A.E., et al., "Human Factor IX Transgenic Sheep Produced by Transfer of Nuclei form Transfected Fetal Fibroblasts," 1997, Science, p. 2130–2133.
Kato, Y., et al., "Eight Calves Cloned from Somatic Cells of a Single Adult," 1998, Science, p. 2095–2098.
Cibelli, J.B., et al. "Cloned Transgenic Calves Produced from Nonquiescent Fetal Fibroblasts," 1998, Science, p. 1256–1258.
Campbell, K.H.S., et al., "Sheep Cloned by Nuclear Transfer from a Cultured Cell Line," 1996, Nature, p. 64–66.

(List continued on next page.)

Primary Examiner—David A. Redding
(74) Attorney, Agent, or Firm—Jones, Tullar & Cooper PC

(57) ABSTRACT

A micro-machined nuclear transfer array (NTA) provides high-throughput transfer of nuclei between two cells. Donor cells containing the nuclei to be transferred are placed in microwells positioned adjacent to microwells containing the recipient biological cell. The microwells are contained within an upper chamber patterned with parallel rows of microwells of the diameter of the cell of interest. An injection port is formed in the bottom of the microwells through which nuclei may pass during transfer. The NTA also contains a lower chamber having a second array of capture wells of similar dimension and in register with the upper chamber for receiving the nuclei removed from the cell in the upper chamber. Nuclei are removed from the donor cells in the upper chamber, transferred to capture wells in the lower chamber, and inserted into the recipient biological cells of the upper chamber. The upper tray moves relative to the lower chamber so that the nuclei in the capture well are transferred to the recipient biological cell to complete the nuclear transfer process.

20 Claims, 4 Drawing Sheets

OTHER PUBLICATIONS

Yanagimachi, R., et al., "Preparation of Nucleate and Enucleate Fragments of Hamster and Mouse Eggs by Centrifugation," 1990, J. Exp. Zool., p. 220–225.

Baguisi, A., et al., "Production of Goats by Somatic Cell Nuclear Transfer," 1999, Nat. Biotech., p. 456–461.

Wakayama, T., et al., "Fertilisablility and Developmental Ability of Mouse Oocytes with Reduced Amounts of Cytoplasm," 1998, Zygote, p. 341–346.

Onishi, A., et al., "Pig Cloning by Microinjection of Fetal Fibroblast Nuclei," Science Magazine, p. 1188–1190, (Aug. 18, 2000).

Polejaeva, I., et al., "Cloned Pigs Produced by Nuclear Transfer from Adult Somatic Cells," Nature Magazine, p. 86–90, (Sep. 7, 2000).

McCreath, K., et al., "Production of Gene–Targeted Sheep by Nuclear Transfer from Cultured Somatic Cells," Nature Magazine, p. 1066–1069, (Jul. 29, 2000).

Tani, T., et al., "Developmental Potential of Cumulus Cell-Derived Cultered Cells Frozen in a Quiescent State After Nucleus Transfer," Theriogeneology, p. 1623–1629, 2000.

Bordignon, V., et al., "Telophase Enucleation: An Improved Method to Prepare Recipient Cytoplasts for Use in Bovine Nuclear Transfer," Molecular Reproduction and Devleopment, p. 29–36, (Jul. 11, 1997).

Singla, S.K., et al., "Micromanipulation and Cloning Studies on Buffalo Oocytes and Embryos Using Nucleus Transfer," Indian Journal of Experimental Biology, p. 1273–1283, (Dec. 30, 1997).

Tatham, B., et al., "Enucleation by Centrifugation of In Vitro–Matured Bovine Oocytes for Use in Nuclear Transfer," Biology of Reporduction, p. 1088–1094, (1995).

* cited by examiner

Centrifugation on density gradient

Cytoplasmic stratification and positioning of nucleus

Cell attachment with patch pipet

Aspiration and patch-enucleation

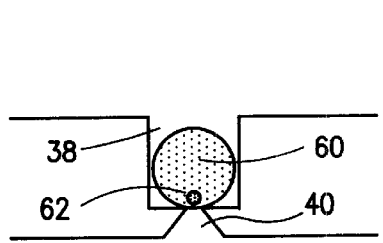
FIG. 4A
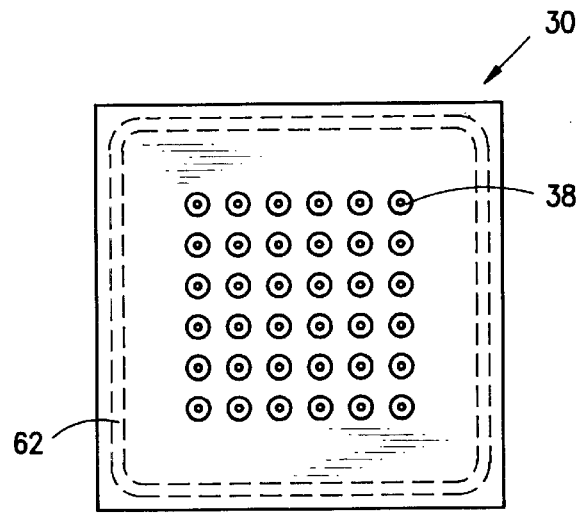
FIG. 4B
FIG. 4C
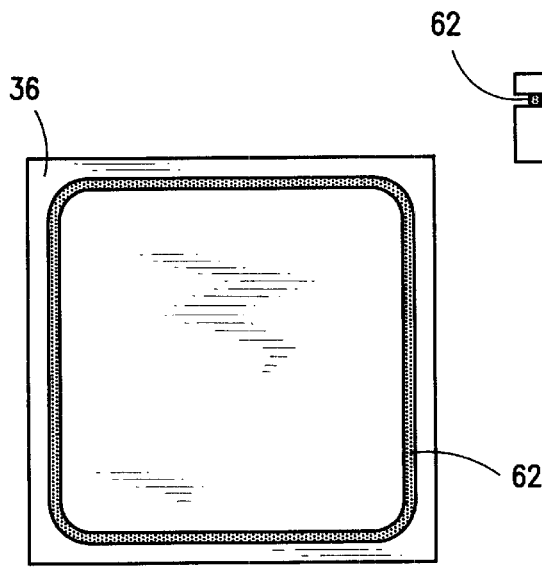
FIG. 5A
FIG. 5B

MICROFABRICATION OF A NUCLEAR TRANSFER ARRAY FOR HIGH-THROUGHPUT ANIMAL CLONING

CROSS REFERENCE TO RELATED APPLICATIONS

This application claims the benefit, under 35 U.S.C. 119(e), of U.S. Provisional Application No. 60/153,677 filed Sep. 14, 1999.

BACKGROUND OF THE INVENTION

Transgenesis, the introduction of foreign gene(s) into a mammalian genome, has its beginnings in the recombinant DNA technology discovered by Boyer and Cohen. By creating the basic tools necessary to directly manipulate DNA, specific genetic modifications at the organismal level was possible. These tools were first applied to simple, unicellular bacteria to both introduce foreign genes and remove endogenous genes but it was quickly realized that these tools were equally applicable to potentially more useful multicellular organisms—e.g. mice, pigs, sheep, goats, and cows. The ability to create transgenic organisms by inserting or deleting specific genes allows one to specify the phenotypic characteristics of the organism—a powerful tool with potentially limitless applications, both commercial and scientific.

Cloning already has demonstrated commercial value, particularly in the production of living "bioreactors", i.e.— transgenic animals expressing therapeutic, pharmaceutically valuable human proteins secreted in milk or urine. As cloning becomes routine, more speculative applications such as transgenic pigs appropriate as a source of organs for xenotransplantation become feasible and potentially could alleviate the current shortage of human donor organs. Moreover, in addition to biomedical applications, transgenic technology will likely have agricultural applications that directly benefit the everyday consumer by improving the disease resistance, growth rate, feed efficiency, and nutritional quality of commercial livestock The recent announcement of Dolly, a sheep cloned from an adult somatic cell, and confirmation of the result in mice, cows, and pigs, has generated intense excitement in the potential of cloning as a greatly improved method for generating transgenic animals. Cloning requires nuclear transfer—the nucleus of the recipient oocyte is removed ("enucleation") and replaced by the nucleus of a donor cell, i.e. the donor nuclei is transferred into a recipient oocyte and the "reconstructed" embryo that develops has the characteristics of the donor individual While nuclear transfer has numerous advantages over pronuclear injection (currently, the most popular method), it is limited by the extremely low efficiency of generating viable offspring (~1–2%)—in a typical series of nuclear transfers, one hundred oocytes result in at most one or two live births which develop into adults. This low efficiency places severe limitations on the commercial use of cloning, especially in domestic animals which have long gestation periods. In addition, nuclear transfer is very technically demanding—microinjection of eggs requires precise manipulations under a high power microscope using expensive micromanipulators and success is often quite dependent on the skill of the operator. Clearly, if the efficiency and/or throughput of nuclear transfer could be improved, the commercial applications become much more feasible and cost-effective.

The low efficiency appears to occur at two points in the nuclear transfer procedure. Following nuclear transfer, only ten to twenty percent of the reconstructed embryos survive to a cell stage that allows them to be implanted in a host. Once implanted, fetal development is often abnormal and most embryos (80–90%) either abort or are stillborn. Improving the low survival rates will require significant research; however an immediate solution is obvious. Currently, nuclear transfer is done serially—i.e. eggs are manipulated individually. If, for example, a thousand or more nuclear transfers could be done simultaneously, the throughput of nuclear transfer increases, minimally, one thousand-fold. Eighty to ninety percent of these embryos, as before, would not survive, but in a given time period the absolute number of implantable embryos (and consequently, transgenic animals) dramatically increases.

SUMMARY OF THE INVENTION

To achieve improved throughput a unique approach which integrates cellular nuclear transfer within a microfabricated silicon-based bioarray has been devised. This nuclear transfer array (NTA) consists of hundreds or thousands of individual nuclear transfer units which, in parallel, will perform the enucleation, transfer, and insertion steps necessary to accomplish nuclear transfer. The advantages of this approach to nuclear transfer will significantly advance adoption of nuclear transfer as a standard technology for producing commercially important transgenic animals and also Father progress in realizing the vast potential of animal cloning in biomedical and agricultural applications.

A micro-machined array (nuclear transfer array, NTA) which allows high-throughput transfer of nuclei between two cells is designed to increase the success of nuclear transfer. A silicon or glass substrate is patterned with parallel rows of cylindrical microwells of the diameter of the cell of interest. A hole is etched in the bottom of the microwell to form an "injection port". This array of microwells forms the top "enucleation" component of the complete NTA. To accomplish nuclear transfer, a bottom or "re-nucleation" component is also necessary. This consists of a second array of microwells of similar dimensions and in register with the top enucleation component. In addition, the re-nucleation component is manufactured with a gasket and outlet which allows vacuum suction to be applied to the complete array. An individual nuclear transfer unit is comprised of the upper enucleation microwell ("upper chamber"), the injection port, and the lower re-nucleation microwell ("lower chamber"). Hundreds to thousands of these nuclear transfer units can be patterned into an individual array.

Individual eggs, oocytes or biological cells are placed into the microwells of the upper chamber. The cells are drawn towards the injection port by centrifugation on a Percoll gradient which centers the nucleus of the cell directly over the injection port and adjacent to the cell membrane. Suction is preferably applied, the membrane is pierced and the nucleus is removed. Nuclei are collected in a lower chamber. Alternatively, nuclei can be purified from cells grown in culture and placed in the wells of the lower chamber. The upper chamber—containing alternating rows of either recipient biological cells or donor biological cells—moves relative to the lower chamber, containing the extracted nuclei. In any case, following enucleation and movement of the upper chamber relative to the lower chamber, the recipient biological cells are positioned in the upper chamber above a donor nucleus. The suction is then reversed resulting in recipient biological cells containing donor nuclei. Alternate means may be used to transfer the nuclei between the upper chamber and lower chamber, including applying electric fields, magnetic fields and centrifugal forces.

The NTA offers a number of advantages over prior nuclear transfer techniques. The NTA is a highly parallel operation such that hundreds to thousands of nuclear transfer (cloning) operations can be done simultaneously with significantly greater throughput than previously possible. The process is automated and therefore should be more reproducible. Most important, the NTA provides a solution to the low efficiency of the cloning process because the absolute number of clones is no longer limiting.

The NTA should be broadly applicable to any use envisioned for cloning. Some applications include producing transgenic animals which express therapeutic, pharmaceutically useful proteins in their milk, generation of non-immunoreactive transgenic pigs for xenotransplantation, development/expansion of superior quality livestock (i.e. higher quality meat, wool, milk, etc.), and individualized creation of human stem cells for replacement therapy. In addition, cloning addresses important scientific questions regarding genomic differention to cancer and aging, and potentially allows the creation of genetic organisms in a more efficient manner and in species other than the mouse.

BRIEF DESCRIPTION OF DRAWINGS

The foregoing and additional features and advantages of the present invention will become apparent to those of skill in the art from the following description of a preferred embodiment thereof taken in conjunction with the accompanying drawings, in which:

FIG. 1A shows the enucleation of the recipient nucleus. FIG. 1B shows the enucleation of the donor nucleus. FIG. 1C shows the nuclear transfer of the donor nucleus into the recipient biological cell.

FIG. 2A. shows the centrigugation on density gradient. FIG. 2B shows the cytoplasmic stratification and positioning of the nucleus. FIG. 2C shows the cell attachment with patch pipet. FIG. 2D shows aspiration and patch-enucleation.

FIG. 3A is an illustration of the cross sectional view of the nuclear transfer array. FIG. 3B is an illustration of the top view of a microwell and enucleation port. FIG. 3C is an illustration of the side view of a microwell and an enucleation port.

FIG. 4A is an illustration of the enucleation component of the nuclear transfer array.

FIG. 4B is an illustration of the top of the preferred embodiment of the nuclear transfer array.

FIG. 4C is an illustration of the cross-section view of the nuclear transfer array.

FIGS. 5A–5B are illustrations of the preferred suction manifold. FIG. 5A is the top view of the preferred suction manifold. FIG. 5B is the side view of the preferred suction manifold.

DETAILED DESCRIPTION OF A PREFERRED EMBODIMENT

Figure 1A:
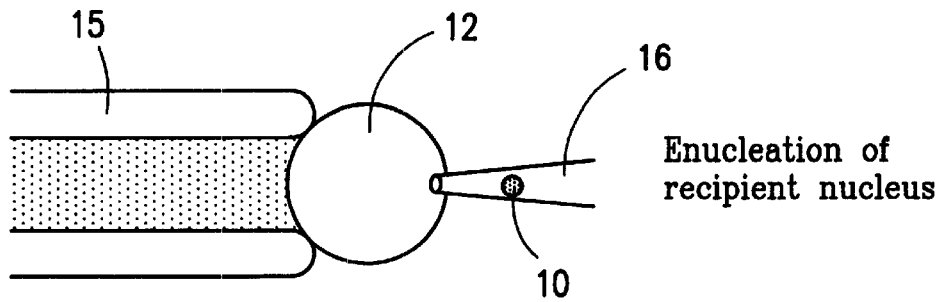
FIGS. 1A–1C are illustrations of a three step nuclear transfer process that can be implemented using a preferred embodiment of the present invention.
Figure 1B:
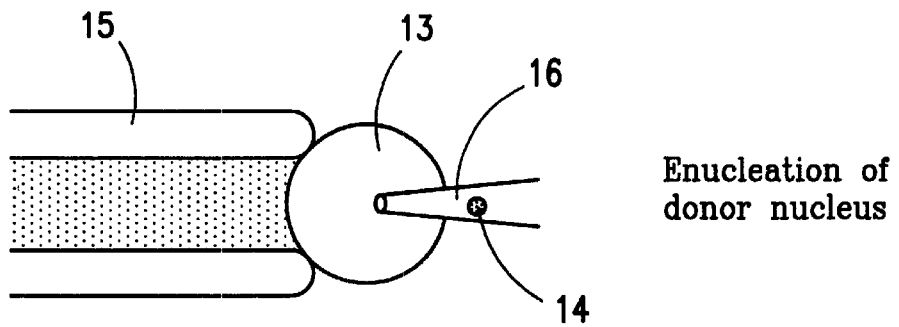
Figure 1C:
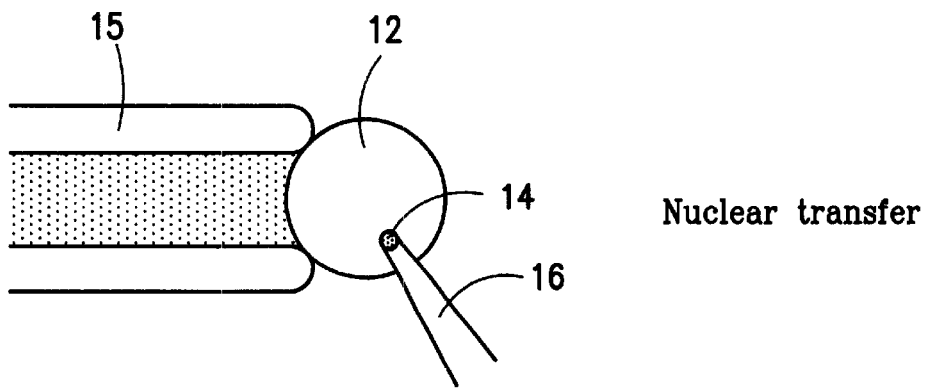

Turning now to a more detailed consideration of the invention, FIGS. 1A–1C illustrate a nuclear transfer technique that can be implemented using a nuclear transfer array (NTA) constructed in accordance with a preferred embodiment of the invention. As illustrated, nuclear transfer is achieved in three steps—(a) enucleation or removal of the recipient nucleus 10 from the recipient biological cell, preferably an oocyte 12, see FIG. 1A; (b) enucleation of the donor nucleus 14 from the donor biological cell 13, see FIG. 1B and (c) transfer of the donor nucleus 14 into the enucleated, recepient oocyte 12, see FIG. 1C. To accomplish this, a suction pipet 15 holds the oocyte 12, or donor biological cell 13, while an injection needle 16 is inserted into the oocyte 12, or donor biological cell 13, to physically remove the recipient nucleus 10, or donor nucleus 14, by aspiration. An additional injection is then needed to insert the donor cell nucleus 14 into the enucleated oocyte 12. Ideally, in operation each nuclear transfer unit of the NTA should faithfully replicate the most efficient method of nuclear transfer available. However, because the physical elements of the NTA are essentially static, a novel approach to nuclear transfer which relies on "patch-enucleation" and controlled vacuum to enucleate and transfer nuclei from donor cell to recipient oocyte has been developed. Additional techniques may be employed to remove the nuclei from the biological cells. The nuclei may be removed by applying an electric field once the cellular membrane has been opened. The nuclei may be labeled with a magnetic label once the cellular membrane has been open and removed by applying a magnetic field. Also, the nuclei may be removed by centrifuging once the cellular membrane has been opened.

Figure 2A:
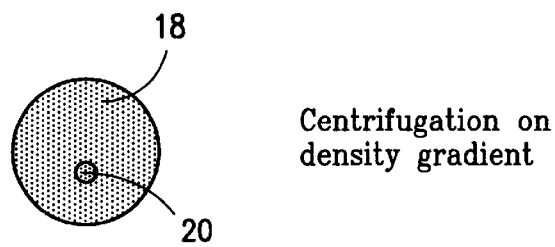
FIGS. 2A–2D are illustrations of a patch-enucleation process that can be implemented using a preferred embodiment of the present invention.
Figure 2B:
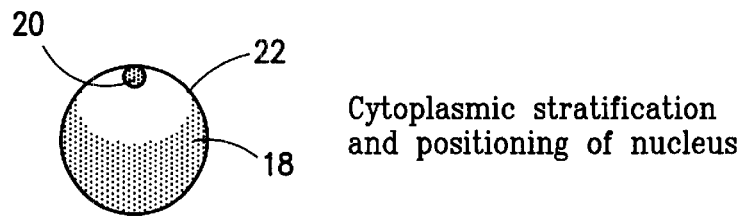
Figure 2C:
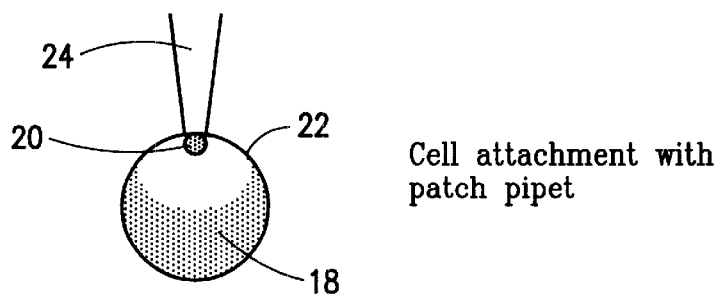
Figure 2D:
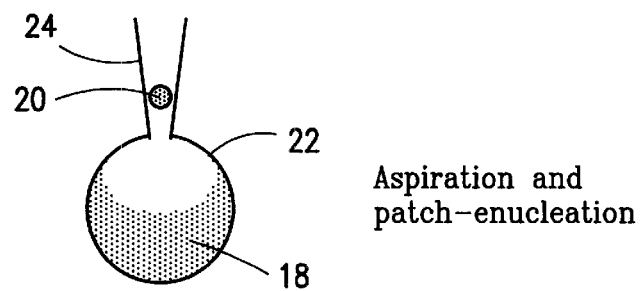

A patch-enucleation process is depicted in FIGS. 2A–2D. In patch-enucleation, oocytes 18 are first centrifuged on a supporting density gradient, as illustrated in FIG. 2A. This results in stratification of the cytoplasm, but most importantly, positioning of the nucleus 20 adjacent to the plasma membrane 22, as illustrated in FIG. 2B. Stratification is reversible and not deleterious to subsequent development. Using techniques analogous to whole-cell patch-clamp recording, a patch-pipet 24 of 5–10 $\mu$m inner diameter is attached to the cell membrane 22 using gentle suction, as illustrated in FIG. 2C. After pipet attachment, increased suction is applied which pierces the membrane 22 and creates continuity between the patch-pipet 24 and the oocyte cytoplasm allowing the nucleus 20 to be removed, as illustrated in FIG. 2D. Incubation in cytochalasin, which disrupts the cytoskeleton, facilitates enucleation and does not affect subsequent development of mammalian oocytes. In experiments using sea urchin eggs, the feasibility of patch-enucleation and renucleation has been demonstrated. This technique greatly decreases the volume of oocyte cytoplasm removed during enucleation, a factor which can be important for later development. An additional benefit is that the opening created during patch-enucleation remains accessible as long as a holding pressure is maintained so that the same opening can be used to re-insert nuclei as opposed to multiple membrane piercing using the microinjection technique.

Figure 3A:
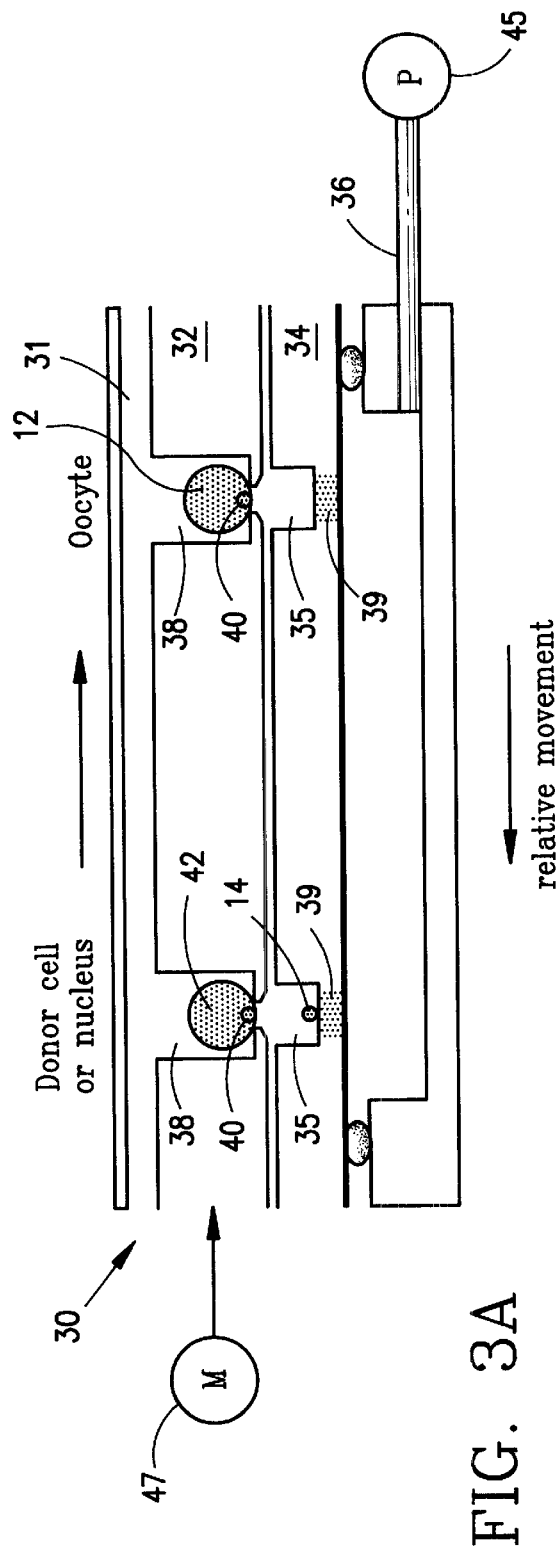
FIGS. 3A–3C are illustrations of the preferred embodiment of the high throughput nuclear transfer array.
Figure 3C:
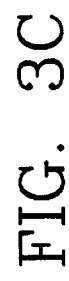
Figure 3B:

To integrate the above described features into the NTA, an array of nuclear transfer units preferably patterned in silicon as parallel rows of etched microwells has been created (roughly the diameter of an oocyte), see FIG. 3A. Alternate compounds may be patterned to form the nuclear transfer array including glass. Each nuclear transfer unit 30 has two components—an upper chamber 32 in which patch-enucleation occurs (enucleation component) and a lower chamber 34 containing capture wells 35 used to capture nuclei removed from recipient oocytes 12 and donor cells 42 (nuclear capture component). A third component of the NTA is a suction manifold 36 connected to a pressure source 45 which allows precise pressure application (both negative and positive) to aspirate and insert nuclei from donor cells 42 and recipient oocytes 12. Although the use of positive pressure and vacuum pressure are the preferred method of aspiring and inserting nuclei alternate methods may be used for aspiring and inserting the nuclei including applying an electric field, magnetic field or centrifugal force to the nuclei. Pressure is applied to the recipient oocyte 12 and donor cells 42 through a porous membrane 39 located at the bottom of the capture wells 35. The upper chamber 32 of the nuclear transfer unit 30 is essentially a microwell 38 with an opening, enucleation port 40, at the base of the well sized to allow nuclei to pass through (either upwards or downwards depending on applied pressure in the suction manifold). FIG. 3B shows a top view of the microwell 38 and enucleation port 40. FIG. 3C shows a side view of the microwell 38 and enucleation port 40.

In actual operation, individual oocytes 12 are pre-treated with cytochalasin and placed in individual upper chambers 32 of each nuclear transfer unit 30 in alternating parallel rows. At this time, donor cells 42 can also be placed in adjacent parallel rows, or alternatively nuclei can be purified from a cell population grown in culture and placed in the bottom, capture chamber. Once the oocytes 12 and donor cells 42 have been loaded, the entire NTA is centrifuged for 30 to 60 minutes at 1000 g, which is sufficient to position the nuclei. As before, suction is preferably applied via the suction manifold 36, the membrane is pierced and the nucleus is removed from the donor cell 42 and retained in the capture well 35. Alternately, an electric field, magnetic field or centrifuge may be used to move the nuclei from the upper chamber 32 to the lower chamber 34. This completes steps (a) and (b) of nuclear transfer—enucleation of the recipient and donor cells. The upper chamber 32—containing alternating rows of either recipient oocytes 12 or donor cells 42—moves relative to the bottom chamber 34, containing the extracted nuclei by means of a micrometer and precisely positioned stop pins 47. In any case, following enucleation and movement of the upper chamber 32 relative to the lower chamber 34, the recipient oocytes 12 are positioned in the upper chamber 32 above a donor nucleus 14 retained in the capture well 35. The suction is then reversed resulting in oocytes 12 containing a transferred donor nucleus 14.

In tests conducted on the preferred embodiment, sea urchin eggs were used as a model system because of experience, the similarities in physical characteristics to mammalian oocytes, and especially the ease and cost of obtaining large quantities of eggs. However, an alternate embodiment would include the use of bovine eggs, with or without zona, as the biological cells. Zona-free bovine eggs are preferably produced using pronase (0.25% at 37 C. for 2–3 min) or acidic Tyrode's solution. This invention is obviously not limited by the type of biological cells used in the nuclear transfer array. A variety of biological cells are envisioned.

Enucleation Component of the NTA
Design

The enucleation device, FIG. 4A, consists of an array of microwells 38 large enough to contain a single egg 60 (e.g., 80 $\mu$m diameter by ~150 $\mu$m deep for sea urchin eggs). At the bottom of each well 38 there is a through-hole, enucleation port 40. The opening of the enucleation port 40 is 4 to 10-$\mu$m in diameter, large enough to allow passage of the nucleus. The device is preferably fabricated in silicon and covered with a No. 2 glass cover slip 31 containing a thin layer of silicone elastomer to serve as a gasket. A suction manifold 36 is constructed out of plastic to accommodate the device.

Enucleation Component Fabrication

The enucleation component of the array is constructed in silicon using standard microfabrication techniques. Start with double polished 3" or 4" silicon wafers with a thin layer of silicon nitride (or thermal oxide) deposited on both sides. A pattern of the microwells 38 and enucleation ports 40 of the array are created using computer assisted design (CAD) software (Cadence). The microwells 38 and the ports 40 are drawn on separate levels and appropriate alignment marks are included. Two chrome photomasks will be generated from this design using a GCA/Mann 3600F Optical Pattern Generator, one containing the array of microwells 38 (Mask 1) and one containing the array of enucleation ports 40 (Mask 2). Using Mask 1, a high-resolution pattern of the microwells 38 is transferred to a silicon nitride coated wafer containing a thin layer (~3 $\mu$m) of positive photoresist (Shipley 1813) deposited on the wafer using a spin coater (4000 rpm for 60 sec). Wafers are exposed to UV light (365 to 405 nm) through the photomask using a Contact Aligner. Following exposure, the photoresist is developed exposing the silicon nitride through the photoresist layer in the defined pattern. The exposed silicon nitride is then etched using a PlasmaTherm PT 72 reactive ion etcher exposing the bare silicon. The microwells 38 are then etched using a PlasmaTherm SLR 770 ICP Deep Silicon Reactive Ion Etch System The nitride is stripped in HF. A 1 $\mu$m thick layer of thermal oxide is grown on the wafer. Next, the enucleation ports 40 are etched from the opposite side of the wafer. This is accomplished by using backside alignment to precisely positioned alignment marks. The steps above are repeated using Mask 2 and the enucleation ports 40 are etched to the oxide, which serves as an etch stop. The ports are opened up by stripping the oxide in HF. The ports can then be reduced in size by depositing an oxide layer. Wet chemical etching, which could have some advantages, may also be used.

Enucleation component prototypes with various size enucleation ports 40 (from ~4 to 10 $\mu$m in diameter) and microwells 38 (from 80 to 150 $\mu$m wide and from ~200 to 300 $\mu$m deep) are fabricated. Prototypes with different array sizes, ranging from a simple row of five to a 100×100 array, are constructed to assist in determining the maximum number of enucleation events that can be accomplish in a single step.

Design of the Suction Manifold

The suction manifold 36 is preferably constructed in Lucite. The overall design is similar to a dot blot apparatus with a depression containing an O-ring 62 to align, hold, and seal the enucleation array 30, as illustrate in FIG. 5A (top view) and FIG. 5B (side view). A deeper depression with a hole and threaded fitting with silicone tubing attached to a suction apparatus is incorporated to provide the suction. Suction is provided via a syringe pump or other means including mouth suction traditionally used in patch-clamp techniques.

Testing the Enucleation Component

The enucleation array prototype was tested using sea urchin eggs. Eggs were incubated with Hoechst 33342 to stain the nuclei. The array was equilibrated with 40% Percoll and eggs were loaded into each well of the array using an embryo transfer pipette. The array was covered with a cover slip 31 containing a thin layer of silicone elastomer (Sylgard 184) to act as a gasket and the assembly was centrifuged with the enucleation ports facing up. After centrifugation, the assembly was placed on a glass microscope slide with the coverslip 31 facing up and the position of the nucleus was determined visually under a fluorescent microscope. The enucleation array was then fitted on the suction manifold. The entire assembly was placed on a fluorescence microscope and mouth suction was applied. Enucleation was monitored using fluorescence microscopy.

Enucleation-Renucleation Prototype

A schematic diagram of the complete enucleation-renucleation prototype is depicted in FIG. 3A. The device consists of the upper 32 and lower 34 chambers and is essentially a complete version of the NTA (but without the capability of the enucleation and nuclear capture components to move relative to each other). The upper chamber 32 is the enucleation component and the lower chamber 34 is the nuclear capture component. The nuclear capture component consists of an array of capture wells 35 fabricated in silicon. The capture wells 35 are positioned directly below each enucleation port 40 of the enucleation component. A porous silicon membrane 39 defines the bottom of the capture wells 35. This entire assembly sits over a suction manifold 36.

Fabricate the Nuclear Capture Component

Fabrication of the nuclear capture component utilizes similar microfabrication techniques described for the fabrication of the enucleation component. The nuclear capture wells 35 are etched using an anisotropic wet etch method. Etching a square feature with KOH will result in a pit with inwardly sloping side walls, approximately 55° to the surface. Various techniques may be used to form the porous silicon 39 on the bottom of these capture wells 35. For example, wet chemical etch with an applied bias or backside illumination has been used successfully to produce porous silicon with holes ranging in diameter from 2 nm to over 10 μm with aspect ratios approaching 250. Alternatively, a polycarbonate membrane (or other material) containing 0.2 μm pores can be affixed to the bottom of the nuclear capture array. Alternatively, a low stress silicon nitride can be deposited to the bottom of the nuclear capture array, and 0.4 μm holes can be etched in this material forming a porous bottom Assemble the Enucleation-renucleation Array Prototype The nuclear capture array will be aligned and bonded to the enucleation array. This assembly is then fitted on the suction manifold. FIG. 4B shows a top view and cross section of the array having microwells 38, O-rings 62 and a suction manifold 36. FIG. 4C shows a cross-section view of the array.

Test Enucleation and Renucleation of Sea Urchin Eggs Using the Array Prototype

Sea urchin eggs were treated as described above and placed in the microwells. The array was centrifuged as described, placed on the suction manifold, and the entire assembly placed on a fluorescence microscope. A suction is applied resulting is removal of the nucleus which is captured in the bottom chamber. The suction is reversed, re-inserting the nucleus into the egg. The cover slip 31 is removed, positive pressure is applied and the egg comes off the injection port.

Although the present invention has been disclosed in terms of a number of preferred embodiments, it will be understood that numerous additional modifications and variations could be made thereto departing from the scope of the invention as defined by the following claims.

What is claimed is:

1. A nuclear transfer array for simultaneously transferring a plurality of nuclei from a plurality of donor biological cells to a plurality of recipient biological cells comprising:
    a) an upper chamber containing a plurality of rows of microwells for receiving a plurality of donor biological cells and a plurality of recipient biological cells in alternating ones of said rows, each of said microwells having a port formed in a bottom thereof;
    b) a lower chamber selectively positioned beneath said upper chamber, said lower chamber containing a plurality of capture wells each having a bottom wall, wherein said capture wells are selectively positionable beneath said ports in said microwells of said upper chamber and movement of said nuclei between said upper chamber and said lower chamber.

2. The nuclear transfer array of claim 1, further comprising a coverslip disposed on said upper chamber.

3. The nuclear transfer array of claim 2, wherein said coverslip is formed from glass.

4. The nuclear transfer array of claim 1, wherein said upper chamber is formed from a material selected from the group comprising silicon and glass.

5. The nuclear transfer array of claim 1, wherein said bottom wall of each of said capture wells is porous.

6. The nuclear transfer array of claim 5, further comprising a suction manifold disposed beneath said lower chamber for supplying a vacuum or a pressure through said porous bottom of said capture wells to facilitate movement of said nuclei between said upper chamber and said lower chamber.

7. The nuclear transfer array of claim 6, wherein said vacuum and said pressure applied to said suction manifold is supplied by a syringe pump.

8. The nuclear transfer array of claim 1, wherein said lower chamber is selectively positionable beneath said upper chamber by a stepper motor.

9. A method for simultaneously transferring a plurality of nuclei from a plurality of donor biological cells to a plurality of recipient biological cells, said method comprising the steps of:
    a) providing an upper chamber containing a plurality of microwells for receiving said donor biological cells and said recipient biological cells wherein each of said microwells has a port formed in a bottom of each of said microwells;
    b) positioning said donor biological cells and said recipient biological cells in each of said microwells in respective alternating parallel rows;
    c) providing a lower chamber positioned beneath said upper chamber containing a plurality of capture wells;
    d) positioning each of said capture wells beneath said port of said upper chamber for receiving said nuclei and wherein each of said capture wells have a bottom;
    e) transferring said nuclei from each of said microwells in said upper chamber through said port of each of said upper chamber to each of said capture wells in said lower chamber;
    f) moving said upper chamber relative to said lower chamber such that said nuclei in each of said capture chamber is positioned beneath each of said microwells containing said recipient biological cell;
    g) transferring said nuclei from each of said capture wells in said lower chamber through said ports to said recipient biological cells in each of said microwells of said upper chamber.

10. The method for transferring a plurality of nuclei of claim 9, wherein the steps of providing an upper chamber and a lower chamber further comprise the step of providing an upper chamber and a lower chamber of a material selected from the group comprising silicon and glass.

11. The method of transferring a plurality of nuclei of claim 9, wherein said bottom of each of said capture wells is porous, and said method further comprises the step of providing a suction manifold for supplying a vacuum or a pressure through said porous bottom of said capture wells to facilitate movement of said nuclei between said upper chamber and said lower chamber.

12. The method for transferring a plurality of nuclei of claim 9, further comprising the step of supplying an electric field to said nuclei to facilitate movement of said nuclei between said upper chamber and said lower chamber.

13. The method for transferring a plurality of nuclei of claim 9, further comprising the step of supplying a magnetic field to said nuclei to facilitate movement of said nuclei between said upper chamber and said lower chamber.

14. The method for transferring a plurality of nuclei of claim 9, further comprising the step of supplying a centrifugal force to said nuclei to facilitate movement of said nuclei between said upper chamber and said lower chamber.

15. The method for transferring a plurality of nuclei of claim 9, wherein said donor biological cells are selected from the group comprising oocytes and purified nuclei.

16. The method for transferring a plurality of nuclei of claim 9, wherein said recipient biological cells are oocytes.

17. The method for transferring a plurality of nuclei of claim 11, wherein the step of providing said suction manifold for supplying said vacuum and said pressure comprises supplying said pressure and said vacuum using a syringe pump.

18. The method for transferring a plurality of nuclei of claim 11, wherein the step of supplying said suction manifold for supplying said vacuum and said pressure comprises supplying said pressure and said vacuum using mouth pressure and suction.

19. The method for transferring a plurality of nuclei of claim 9, wherein the step of moving said upper chamber relative to said lower chamber comprises moving said upper chamber relative to said lower chamber using a stepper motor.

20. The method for transferring a plurality of nuclei of claim 9, wherein the step of moving said upper chamber relative to said lower chamber comprises moving said upper chamber relative to said lower chamber using manual motion of a micrometer.

* * * * *

UNITED STATES PATENT AND TRADEMARK OFFICE
CERTIFICATE OF CORRECTION

PATENT NO. : 6,383,813 B1
DATED : May 7, 2002
INVENTOR(S) : Gregory T. Baxter et al.

It is certified that error appears in the above-identified patent and that said Letters Patent is hereby corrected as shown below:

<u>Column 8,</u>
Line 8, replace "chamber and" with -- chamber and said ports in said microwells are constructed to separate the nuclei from the donor cell and facilitate --.

Signed and Sealed this

Twenty-ninth Day of October, 2002

Attest:

Attesting Officer

JAMES E. ROGAN
Director of the United States Patent and Trademark Office